United States Patent
Hase et al.

(10) Patent No.: US 9,353,204 B2
(45) Date of Patent: May 31, 2016

(54) (METH)ACRYLATE COMPOSITION

(71) Applicants: AUTONETWORKS TECHNOLOGIES, LTD., Yokkaichi-shi, Mie (JP); SUMITOMO WIRING SYSTEMS, LTD., Yokkaichi-shi, Mie (JP); SUMITOMO ELECTRIC INDUSTRIES, LTD., Osaka-shi, Osaka (JP); KYUSHU UNIVERSITY, Fukuoka-shi, Fukuoka (JP)

(72) Inventors: Tatsuya Hase, Yokkaichi (JP); Kazuo Nakashima, Yokkaichi (JP); Makoto Mizoguchi, Kasuga (JP)

(73) Assignees: AUTONETWORKS TECHNOLOGIES, LTD., Mie (JP); SUMITOMO WIRING SYSTEMS, LTD., Mie (JP); SUMITOMO ELECTRIC INDUSTRIES, LTD., Osaka (JP); KYUSHU UNIVERSITY, Fukuoka (JP)

(*) Notice: Subject to any disclaimer, the term of this patent is extended or adjusted under 35 U.S.C. 154(b) by 0 days.

(21) Appl. No.: 14/429,598

(22) PCT Filed: Aug. 9, 2013

(86) PCT No.: PCT/JP2013/071647
§ 371 (c)(1),
(2) Date: Mar. 19, 2015

(87) PCT Pub. No.: WO2014/054343
PCT Pub. Date: Apr. 10, 2014

(65) Prior Publication Data
US 2015/0232591 A1    Aug. 20, 2015

(30) Foreign Application Priority Data

Oct. 2, 2012    (JP) ................. 2012-220492

(51) Int. Cl.
| | | |
|---|---|---|
| *C08F 2/46* | (2006.01) | |
| *C08F 20/22* | (2006.01) | |
| *C08G 61/04* | (2006.01) | |
| *C08F 122/10* | (2006.01) | |
| *C07C 69/54* | (2006.01) | |
| *C07D 307/16* | (2006.01) | |
| *C07C 69/602* | (2006.01) | |
| *C08F 120/12* | (2006.01) | |
| *C08F 120/14* | (2006.01) | |
| *C08F 120/28* | (2006.01) | |
| *C08F 120/20* | (2006.01) | |

(52) U.S. Cl.
CPC ............. *C08F 122/105* (2013.01); *C07C 69/54* (2013.01); *C07C 69/602* (2013.01); *C07D 307/16* (2013.01); *C08F 120/12* (2013.01); *C08F 120/14* (2013.01); *C08F 120/20* (2013.01); *C08F 120/28* (2013.01)

(58) Field of Classification Search
CPC .. C08F 122/105; C08F 120/12; C08F 120/28; C08F 120/14; C08F 120/20; C07D 307/16; C07C 69/54; C07C 69/602
USPC .................................. 522/182, 178, 1; 520/1
See application file for complete search history.

(56) References Cited

U.S. PATENT DOCUMENTS

| | | | | |
|---|---|---|---|---|
| 4,303,485 A * | 12/1981 | Levens | ................ | C08F 2/46 427/516 |
| 4,421,822 A | 12/1983 | Levens | | |
| 2003/0032692 A1* | 2/2003 | Mejiritski | ............ | C09D 11/101 522/173 |
| 2005/0196605 A1 | 9/2005 | Ramsey | | |
| 2011/0021655 A1 | 1/2011 | Smothers et al. | | |
| 2012/0010316 A1 | 1/2012 | Meyer et al. | | |
| 2012/0112456 A1 | 5/2012 | Nagareo et al. | | |
| 2012/0231234 A1 | 9/2012 | Kodama | | |
| 2013/0338327 A1 | 12/2013 | Hase et al. | | |

FOREIGN PATENT DOCUMENTS

| | | |
|---|---|---|
| EP | 2228414 A1 | 9/2010 |
| JP | S56-30410 A | 3/1981 |
| JP | S57-177008 A | 10/1982 |
| JP | H03-84011 A | 4/1991 |
| JP | H04-11610 A | 1/1992 |
| JP | H04-220485 A | 8/1992 |
| JP | H07-11215 A | 1/1995 |
| JP | H08-104705 A | 4/1996 |
| JP | 2004/346124 A | 12/2004 |
| JP | 2009-292936 A | 12/2009 |

(Continued)

OTHER PUBLICATIONS

Arkon P-115, http://www.arakawaeurope.com/pdfs/PDS%20P115-1206.pdf, May 2000.*
Sep. 3, 2013 International Search Report issued in International Patent Application No. PCT/JP2013/071647.

(Continued)

*Primary Examiner* — Ling Choi
*Assistant Examiner* — Jessica E Whiteley
(74) *Attorney, Agent, or Firm* — Oliff PLC

(57) ABSTRACT

Presented is a (meth)acrylate composition that can be cured even in an unirradiated portion that is not reached by light. The (meth)acrylate composition contains a compound having one or more vinyl groups in a molecular structure thereof. The compound has a ratio of a molecular weight thereof to a number of the vinyl groups of 300 or lower. The composition generates a heat of reaction during photopolymerization thereof, and the heat of reaction causes thermal polymerization of the composition.

3 Claims, No Drawings

(56) References Cited

FOREIGN PATENT DOCUMENTS

| | | |
|---|---|---|
| JP | 2011-012251 A | 1/2011 |
| JP | 2011-508814 A | 3/2011 |
| JP | 2012-186356 A | 9/2012 |
| JP | 2012-520355 A | 9/2012 |
| WO | 2010/140703 A1 | 12/2010 |
| WO | 2012/102299 A1 | 8/2012 |

OTHER PUBLICATIONS

Dec. 28, 2015 Office Action issued in Chinese Application No. 201380051451.1.

Mar. 15, 2016 extended European Search Report issued in Application No. 13843751.2.

Mar. 18, 2016 Office Action issued in Japanese Application No. 2012-220492.

* cited by examiner

(METH)ACRYLATE COMPOSITION

TECHNICAL FIELD

The present invention relates to a (meth)acrylate composition suitably used as a material for adhesion, coating, sealing, and molding in automobile components, electric/electronic devices, and aircraft components.

BACKGROUND ART

Conventionally, a (meth)acrylate composition is known that contains a chain transfer agent, a urethane (meth)acrylate having a plurality of ethylenic unsaturated bonds, a meth (acrylate) monomer, a thermal polymerization initiator, and a photopolymerization initiator (see PTL1).

The composition can be cured by exposure to thermal energy or to an actinic ray (such as an ultraviolet ray) and thermal energy in combination.

CITATION LIST

Patent Literature

Patent Literature 1: JP 2011-508814 A

SUMMARY OF INVENTION

Technical Problem

Radicals are involved in the curing reaction of the composition described above. Radicals have a high activity, but are deactivated instantaneously, having short lives. Though a certain amount of radicals can cause a chain reaction, the curing reaction proceeds only in the close vicinity where radicals are generated. Thus, if the composition has a dark portion that is not irradiated with light sufficiently, the composition is not sufficiently cured in the vicinity of the dark portion, and thus does not fully work as a curable material. Therefore, the composition is difficult to be cured homogeneously including a portion hardly reached by light by photocuring alone. Exposure to the thermal energy or to the actinic energy and the thermal energy in combination is necessary. A mechanism of curing should be introduced by which the composition is cured homogeneously including the portion hardly reached by light by photocuring alone.

An object of the present invention is to overcome the problems in the conventional technique described above and to provide a (meth)acrylate composition that can be cured even in an unirradiated portion that is not reached by light.

Solution to Problem

To achieve the object and in accordance with the purpose of the present invention, a (meth)acrylate composition contains a first compound having one or more vinyl groups in a molecular structure thereof, the first compound having a ratio of a molecular weight thereof to a number of the vinyl groups of 300 or lower, wherein the composition generates a heat of reaction during photopolymerization thereof, and the heat of reaction causes thermal polymerization of the composition.

The composition is curable in a portion that is not irradiated with light by the thermal polymerization induced by the photopolymerization.

It is preferable that the composition further comprises one or more vinyl group-containing compounds other than the first compound, including a second compound having one or more vinyl groups in a molecular structure thereof, the second compound having a ratio of a molecular weight thereof to a number of the vinyl groups higher than 300, and that a content of the first compound with respect to a total content of all vinyl group-containing compounds in the composition is 30 mass % or higher.

It is also preferable that the composition further comprises 0.1 to 20 mass % of a photopolymerization initiator with respect to a total mass of the composition.

Advantageous Effects of Invention

A (meth)acrylate undergoes a self-polymerization reaction at a certain temperature in a range of 130 to 150° C., or higher. A photopolymerization reaction of the (meth)acrylate is an exothermic reaction. When the photopolymerization reaction occurs at a larger number of reaction sites in a certain volume during a certain period, a larger amount of exothermic heat is generated. Since a volume occupied by a molecule substantially depends on a molecular weight thereof, and since vinyl groups serve as the reaction sites for the polymerization, a (meth)acrylate having a larger number of vinyl bonds in a certain molecular weight generates a larger amount of heat of reaction during the photopolymerization. When the temperature of the (meth)acrylate rises above the starting temperature of the self-polymerization thereof, the (meth)acrylate is cured by the self-polymerization even in a portion that is not reached by light.

The (meth)acrylate composition according to the preferred embodiment of the present invention contains the (meth)acrylate compound having the ratio of the molecular weight thereof to the number of the vinyl groups of 300 or lower so that the compound has a certain density of the vinyl groups, which generates the heat of reaction. Thus, the (meth)acrylate compound can be thermally polymerized even in a portion that is not reached by light.

DESCRIPTION OF EMBODIMENTS

A detailed description of a preferred embodiment of the present invention will now be provided. A ratio of a molecular weight to a number of vinyl groups (i.e., 'molecular weight/number of vinyl groups') of a (meth)acrylate ingredient in a (meth)acrylate composition according to a preferred embodiment of the present invention denotes a value obtained by division of a theoretical molecular weight based on a structural formula of the (meth)acrylate ingredient by the number of the vinyl groups.

If the ratio 'molecular weight/number of vinyl groups' of the (meth)acrylate ingredient is higher than 300, the density of the vinyl groups, which generate heat of reaction, could be too low to provide sufficient heat of reaction to cause polymerization of the composition in a portion that is not reached by light. On the other hand, when the ratio is 300 or lower, the portion can be heated up to a starting temperature for self-polymerization or higher by the heat of reaction. The composition may further contain another vinyl group-containing compound [i.e., another (meth)acrylate ingredient] having a ratio 'molecular weight/number of vinyl groups' higher than 300.

When the content of the (meth)acrylate ingredient having the ratio 'molecular weight/number of vinyl groups' of 300 or lower is at a certain level or higher with respect to a total mass of the composition, exothermic heat sufficient to start the self-polymerization reaction is generated, and the composition is effectively cured in the portion that is hardly reached by light. To be specific, the content of the (meth)acrylate ingredient having the ratio 'molecular weight/number of vinyl groups' of 300 or lower is preferably 30 mass % or higher with respect to a total content of all vinyl group-containing compounds, to generate sufficient heat of reaction and to polymerize the portion that is not reached by light. The content of the (meth)acrylate ingredient having the ratio 'molecular weight/number of vinyl groups' higher than 300 is preferably lower than 70 mass % with respect to the total content of the all vinyl group-containing compounds.

The upper limit of the content of the (meth)acrylate ingredient having the ratio 'molecular weight/number of vinyl groups' of 300 or lower is 100 mass % with respect to the total content of the all vinyl group-containing compounds in the composition.

The types of the (meth)acrylate ingredients are not limited specifically as long as containing one or more (meth)acrylate groups in each molecular structure thereof. Thus, conventionally known (meth)acrylate monomers, oligomers, and polymers may be used. The term "(meth)acrylate" refers to both an acrylate and a methacrylate in the present invention.

Specific examples of the (meth)acrylate include mono (meth)acrylates such as isobornyl (meth)acrylate, bornyl (meth)acrylate, tricyclodecanyl (meth)acrylate, dicyclopentanyl (meth)acrylate, dicyclopentenyl (meth) acrylate, cyclohexyl (meth)acrylate, (meth) acrylic acid, benzyl (meth)acrylate, 4-butylcyclohexyl (meth)acrylate, (meth)acryloylmorpholine, 2-hydroxyethyl (meth)acrylate, 2-hydroxypropyl (meth)acrylate, 4-hydroxybutyl (meth)acrylate, methyl (meth)acrylate, ethyl (meth)acrylate, propyl (meth)acrylate, isopropyl (meth)acrylate, octyl (meth)acrylate, isooctyl (meth)acrylate, nonyl (meth)acrylate, decyl (meth)acrylate, isodecyl (meth)acrylate, undecyl (meth)acrylate, dodecyl (meth)acrylate, lauryl (meth)acrylate, stearyl (meth)acrylate, isostearyl (meth)acrylate, tetrahydrofurfuryl (meth)acrylate, poly(ethylene glycol) mono(meth)acrylate, poly(propylene glycol) mono(meth)acrylate, methoxyethylene glycol (meth)acrylate, ethoxyethyl (meth)acrylate, methoxypolyethylene glycol (meth)acrylate, methoxypolypropylene glycol (meth)acrylate, polyoxyethylene nonylphenyl ether acrylate, diacetone (meth) acrylamide, isobutoxymethyl (meth) acrylamide, N,N-dimethyl (meth)acrylamide, t-octyl (meth)acrylamide, dimethylaminoethyl (meth)acrylate, diethylaminoethyl (meth) acrylate, 7-amino-3,7-dimethyloctyl (meth)acrylate, N,N-diethyl (meth)acrylamide, and N,N-dimethyl aminopropyl (meth)acrylamide; and poly (meth)acrylates such as butanediol di(meth)acrylate, hexanediol di(meth)acrylate, nonanediol di(meth)acrylate, decanediol di(meth)acrylate, 2-butyl-2-ethyl-1,3-propanediol di(meth)acrylate, 2-hydroxy-3-acryloyloxy propyl methacrylate, dipropylene glycol di(meth)acrylate, tripropylene glycol di(meth)acrylate, triethylene glycol di(meth)acrylate, tetraethylene glycol di(meth)acrylate, tricyclodecane dimethylol di(meth)acrylate, 1,4-butanepolyoldi(meth)acrylate, 1,6-hexanepolyol di(meth)acrylate, neopentyl glycol di(meth)acrylate, polyethylene glycol di(meth)acrylate, polypropylene glycol di(meth)acrylate, 9,9-bis[4-(2-acryloyloxyethoxy)phenyl]fluorine, polyester di(meth)acrylate, tris(2-hydroxyethyl) isocyanurate tri(meth)acrylate, tris-(2-hydroxyethyl) isocyanurate di(meth)acrylate, tricyclodecane dimethylol di(meth)acrylate, di(meth)acrylate of EO-added bisphenol A, di(meth)acrylate of polyol of EO- or PO-added hydrogenated bisphenol A, an epoxy (meth)acrylate obtained by addition of a (meth)acrylate to diglycidylether of bisphenol A, triethylene glycol divinyl ether, trimethylolpropane tri(meth)acrylate, pentaerythritol tri (meth)acrylate, EO-added trimethylolpropane tri(meth)acrylate, tris-acryloyloxyethyl phosphate, pentaerythritol tetra (meth)acrylate, tetrafurfuryl alcohol oligo(meth)acrylate, ethyl carbitol oligo(meth)acrylate, 1,4-butanediol oligo (meth)acrylate, 1,6-hexanediol oligo(meth)acrylate, trimethylolpropane oligo(meth)acrylate, pentaerythritol oligo (meth)acrylate, (poly)urethane (meth)acrylate, and (poly) butadiene (meth)acrylate. They may be used singly or in combination.

The (meth)acrylate composition may contain a Photopolymerization initiator (i.e., a photoinitiator). Any photoinitiator that initiates photopolymerization may be used. Specific examples of the photoinitiator include 1-hydroxycyclohexyl phenyl ketone, 2,2-dimethoxy-2-phenylacetophenone, xanthone, fluorenone, benzaldehyde, fluorene, anthraquinone, ethylanthraquinone, triphenylamine, carbazole, 3-methylacetophenone, 4-chlorobenzophenone, 4,4'-dimethoxybenzophenone, 4,4'-diaminobenzophenone, Michler's ketone, benzoin propyl ether, benzoin ethyl ether, benzil dimethylketal, 1-(4-isopropylphenyl)-2-hydroxy-2-methylpropane-1-one, 2-hydroxy-2-methyl-1-phenylpropane-1-one, thioxanthone, diethylthioxanthone, 2-isopropylthioxanthone, 2-chlorothioxanthone, 2-methyl-1-[4-(methylthio)phenyl]-2-morpholino-pr opane-1-one, 2,4,6-trimethyl benzoyl diphenyl phosphine oxide, and bis-(2,6-dimethoxy benzoyl)-2,4,4-trimethylpentyl phosphine oxide. They may be used singly or in combination.

Examples of commercial products that may be used as the photoinitiator include IRGACUREs 184, 369, 651, 500, 907, CGI1700, CGI1750, CGI1850, and CG24-61; DAROCUREs 1116 and 1173; LucirinTPO (all manufactured by BASF); and EBECRYL P36 (manufactured by UCB).

The content of the photoinitiator is preferably within a range of 0.1 to 20 mass % with respect to the total mass of the composition.

The composition may further contain various kinds of additives as necessary within a range of not impairing the object of the present invention. Examples of the additives include a stabilizer, a plasticizer, a softener, a pigment, a dye, an antistatic agent, a flame retardant, a sensitizer, a dispersing agent, a solvent, an antibacterial agent, and a fungicide.

Examples of the stabilizer include an antiaging agent, an antioxidant, and a dehydrating agent. Specific examples of the stabilizer include an antiaging agent such as a hindered phenol compound and a hindered amine compound, an antioxidant such as butylhydroxytoluene, butylhydroxyanisole, and triphenyl phosphite, and a dehydrating agent such as maleic anhydride, phthalic anhydride, benzophenonetetracarboxylic dianhydride, calcined lime, a carbodiimide derivative, and an acid chloride such as stearic acid chloride. A small amount of a polymerization inhibitor such as methoquinone may also be used as the stabilizer. It is to be noted that most of the stabilizers described above have negative influences on the reaction in which free radicals are involved, so that it is preferable that the stabilizers are added to the material only in a small amount.

Examples of the plasticizer include dioctyl adipate, dibutyl sebacate, diethylhexyl sebacate, isodecyl succinate, diethylene glycol dibenzoate, pentaerythritol ester, butyl oleate, methyl acetyl ricinolate, tricresyl phosphate, trioctyl phosphate, propylene adipate glycol polyester, butylene adipate glycol polyester, phenol, lauric acid, stearic acid, docosanoic acid, a paraffinic oil, a napthenic oil, and an aromatic oil.

Examples of the softener include a vinyl group-containing lactam such as N-vinyl pyrrolidone and N-vinylcaprolactam, hydroxyl butyl vinyl ether, lauryl vinyl ether, cetyl vinyl ether, and 2-ethylhexyl vinyl ether.

Examples of the pigment include an inorganic pigment such as titanium dioxide, zinc oxide, ultramarine, colcothar, lithopone, lead, cadmium, iron, cobalt, aluminum, a hydrochloride salt, and a sulfate salt, and an organic pigment such as an azo pigment and a copper phthalocyanine pigment.

Examples of the antistatic agent include a hydrophilic compound such as quaternary ammonium salt, polyglycol, and an ethylene oxide derivative.

Examples of the flame retardant include chloroalkyl phosphate, dimethyl methyl phosphonate, a bromine/phosphorous compound, ammonium polyphosphate, neopentylbromide-polyether, and brominated polyether.

Examples of the sensitizer include dimethylformamide,N-methylpyrrolidone,triethylamine, diethylamine, N-methyldiethanolamine, ethanolamine, 4-dimethylaminobenzoic acid, methyl 4-dimethylamino benzoate, ethyl 4-dimethylamino benzoate, isoamyl 4-dimethylamino benzoate, and commercial products such as EBECRYL P102, 103, 104 and 105 (manufactured by UCB).

Examples of the dispersing agent include a surfactant such as polyoxyethylene nonylphenyl ether and polyethylene glycol octylphenyl ether.

Examples of the solvent include any solvent as long as the solvent dissolves a molecular complex to reduce the viscosity thereof, or to increase the compatibility thereof. Specific examples of the solvent include a polar solvent such as tetrahydrofuran, dimethylformamide, ethyl acetate, and methyl ethyl ketone, and a chlorine containing solvent such as dichloroethane and trichlorobenzene.

An entire portion of the (meth)acrylate composition according to the preferred embodiment of the present invention can be cured by photopolymerization and thermal polymerization when irradiated with light such as ultraviolet from an irradiation device. Visible light may also be used as well as ultraviolet light for the irradiation. A variety of conventionally known irradiation devices may be used for the ultraviolet irradiation. The conditions for the ultraviolet irradiation may be determined as appropriate, for example, in accordance with a shape of the composition.

The (meth)acrylate composition according to the preferred embodiment of the present invent ion may be used, for example, as a material for adhesion, coating, sealing, and molding in automobile components, electric/electronic devices, and aircraft components. Since the composition can be thermally polymerized in a portion that is not irradiated with light induced by the photopolymerization thereof, the resin can be cured even in a dark portion that is not reached by light. Thus, the resin is most suitably used for a part that has a dark portion and is hard to be heated.

EXAMPLE

A description of the present invention will now be specifically provided with reference to examples and comparative examples; however, the present invention is not limited to the examples.

Examples 1 to 15 and Comparative Example 1 to 4

[Preparation of Compositions]

The ingredients shown in Tables 1 to 3 were mixed with an agitation equipment in the content ratios shown in the tables (in part by mass), and were dissolved or dispersed in each other. Thus, the compositions shown in the tables were prepared. Abbreviations described below are used in the tables. Reagents with no specific indication of manufacturers are reagent-grade products manufactured by TOKYO CHEMICAL INDUSTRY CO., LTD. The ratios 'molecular weight/number of vinyl groups' of the (meth)acrylates are also shown in the tables.

<(Meth)acrylate>
IBA: isobornyl acrylate
IBMA: isobornyl methacrylate
HEA: hydroxyethyl acrylate
HPA: hydroxypropyl acrylate
THFA: tetrafurfuryl acrylate
EEEA: 2-(2-ethoxyethoxy)ethyl acrylate
EHA: ethylhexyl acrylate
DPGA: dipropylene glycol diacrylate
TEGA: tetraethylene glycol diacrylate
TMPTA: trimethylolpropane triacrylate
TMPEOA: trimethylolpropane EO-added triacrylate, manuf.: OSAKA ORGANIC CHEMICAL INDUSTRY LTD.
APG400: polypropylene glycol (#400) diacrylate, manuf.: SHIN-NAKAMURA CHEMICAL CO., LTD.
STA: stearyl acrylate
BPADA: bisphenol-A ethoxy diacrylate, manuf.: SIGMA-ALDRICH CORPORATION
APG700: polypropylene glycol (#700) diacrylate, manuf.: SHIN-NAKAMURA CHEMICAL CO., LTD.
UP-1: a synthetic compound (synthesis example will be described later)
<Photoinitiator>
HCHPK: 1-hydroxycyclohexyl phenyl ketone Synthesis Example 1

Synthesis of UP-1

80 g (200 mmol) of polypropylene glycol having a number-average molecular weight of 400, 40 g (238 mmol) of hexamethylene diisocyanate, and 0.05 g of dibutyltin dilaurate were put in a reaction container with an agitation equipment, and the liquid was heated up to 50° C. from room temperature in one hour while agitated. Then, while a small amount of the mixture was sampled for FT-IR measurement to check absorption of an isocyanate group in the vicinity of 2300 cm$^{-1}$, the agitation was continued at 50° C. The content of the residual isocyanate group was calculated based on the absorption area of FT-IR. The moment when the content of the residual isocyanate group decreased down to about 15% compared with the content before the reaction and no change was seen was regarded as an the completion of the reaction. Thus, a clear and colorless viscous liquid was obtained. Further, 9.84 g (84.8 mmol) of 2-hydroxyethyl acrylate, 0.05 g of dibutyltin dilaurate, and 0.02 g of pentaerythritol tetrakis [3-(3,5-di-tert-butyl-4-hydroxyphenyl)pro pionate] were put in the liquid, and the mixture was heated up to 50° C. from room temperature in one hour while agitated. Then, while a small amount of the mixture was sampled for FT-IR measurement to check absorption of an isocyanate group in the vicinity of 2300 cm$^{-1}$, the agitation was continued at 50° C. The content of the residual isocyanate group was calculated based on the absorption area of FT-IR. The moment when the absorption disappeared was regarded as the completion of the reaction. Thus, a clear and colorless viscous liquid was obtained. The obtained liquid is called UP-1 . UP-1 is a urethane acrylate having acrylate groups at both terminals. UP-1 has a number-average molecular weight of approximately 3200.

[Measurement of Curability in Unirradiated Portion]

Each of the compositions was put in a glass tube having an inner diameter of 5 mm and a height of 50 mm such that the liquid level was 20 mm high. The upper half (10 mm) of the content in the glass tube was wrapped with an aluminum foil to make a light-shielded portion. Then, the composition was irradiated with ultraviolet for 50 seconds from the side with the use of a UV lamp (100 mW/cm$^2$, manufactured by SEN LIGHTS CO., LTD.). Then, the glass tube was left for 20 minutes at room temperature to return the composition to room temperature. Then, a glass rod having a diameter of 1.5 mm was inserted from the top of the glass tube, and the cured product was detected by touching with the rod. Thus, a length at which formation of the cured product had proceeded upward (i.e., into an unirradiated portion) from the border between the ultraviolet-irradiated portion and the light-shielded portion was measured. Measurement results are presented in Tables 1 to 3.

[Measurement of Temperature in Unirradiated Portion]

Each of the compositions was put in a glass tube having an inner diameter of 5 mm and a height of 50 mm such that the liquid level was 20 mm high. The upper half (10 mm) of the content in the glass tube was wrapped with an aluminum foil to make a light-shielded portion. Then, the composition was irradiated with ultraviolet for 50 seconds from the side with the use of a UV lamp (100 mW/cm$^2$, manufactured by SEN LIGHTS CO., LTD.). During the irradiation, a temperature in the light-shielded portion was measured with the use of a contactless thermometer. Measurement results are presented in Tables 1 to 3.

[Assessment of Curability in Unirradiated Portion]

Since the (meth)acrylates contained in the compositions according to Comparative Examples 1 to 4 have the ratios 'molecular weight/number of vinyl groups' higher than 300, sufficient heats were not generated during the polymerization. Thus, the temperatures in the light-shielded portions were 120° C. or lower, and the curing hardly proceeded in the unirradiated portions. Meanwhile, in Examples 1 to 15, the temperatures in the light-shielded portions were 150° C. or higher. Thus, the compositions according to Examples are cured even in unirradiated portions by photoirradiation alone.

TABLE 1

| | | Mol. Weight/ Num. of Vinyl Gps. | Example 1 | 2 | 3 | 4 | 5 | 6 | 7 | 8 |
|---|---|---|---|---|---|---|---|---|---|---|
| (Meth)acrylate | IBA | 208 | 100 | | | | | | | |
| | IBMA | 222 | | 100 | | | | | | |
| | HEA | 116 | | | 100 | | | | | |
| | HPA | 130 | | | | 100 | | | | |
| | THFA | 156 | | | | | 100 | | | |
| | EEEA | 188 | | | | | | 100 | | |
| | EHA | 184 | | | | | | | 100 | |
| | DPGA | 120 | | | | | | | | 100 |
| | TEGA | 156 | | | | | | | | |
| | TMPTA | 98 | | | | | | | | |
| | TMPEOA | 150 | | | | | | | | |
| | APG400 | 268 | | | | | | | | |
| | STA | 324 | | | | | | | | |
| | BPADA | 344 | | | | | | | | |
| | APG700 | 404 | | | | | | | | |
| | UP-1 | 1600 | | | | | | | | |
| Photoinitiator | HCHPK | | 2 | 2 | 2 | 2 | 2 | 2 | 2 | 2 |
| Temperature in light-shielded portion(° C.) | | | 160 | 157 | 168 | 165 | 165 | 163 | 165 | 169 |
| Length of cured product in unirradiated portion (mm) | | | 2.4 | 2.1 | 3.5 | 5.4 | 3.2 | 3.9 | 2.1 | 4.8 |

TABLE 2

| | | Mol. Weight/ Num. of Vinyl Gps. | Example 9 | 10 | 11 | 12 | 13 | 14 | 15 |
|---|---|---|---|---|---|---|---|---|---|
| (Meth)acrylate | IBA | 208 | | | | | | | |
| | IBMA | 222 | | | | | | | |
| | HEA | 116 | | | | | | | |
| | HPA | 130 | | | | | | | |
| | THFA | 156 | | | | | | | |
| | EEEA | 188 | | | | | | | |
| | EHA | 184 | | | | | | | |
| | DPGA | 120 | | | | | 50 | | 30 |
| | TEGA | 156 | 100 | | | | | | |
| | TMPTA | 98 | | 100 | | | | | |
| | TMPEOA | 150 | | | 100 | | | | |
| | APG400 | 268 | | | | 100 | | 50 | |
| | STA | 324 | | | | | | | |
| | BPADA | 344 | | | | | | | |
| | APG700 | 404 | | | | | | | |
| | UP-1 | 1600 | | | | | 50 | 50 | 70 |
| Photoinitiator | HCHPK | | 2 | 2 | 2 | 2 | 2 | 2 | 2 |
| Temperature in light-shielded portion(° C.) | | | 162 | 175 | 164 | 158 | 161 | 151 | 153 |
| Length of cured product in unirradiated portion (mm) | | | 4.1 | 5.1 | 4.5 | 2.2 | 3.1 | 2.1 | 2.8 |

TABLE 3

| | | Mol. Weight/Num. of Vinyl Gps. | Comparative Example 1 | 2 | 3 | 4 |
|---|---|---|---|---|---|---|
| (Meth)acrylate | IBA | 208 | | | | |
| | IBMA | 222 | | | | |
| | HEA | 116 | | | | |
| | HPA | 130 | | | | |
| | THFA | 156 | | | | |
| | EEEA | 188 | | | | |
| | EHA | 184 | | | | |
| | DPGA | 120 | | | | |
| | TEGA | 156 | | | | |
| | TMPTA | 98 | | | | |
| | TMPEOA | 150 | | | | |
| | APG400 | 268 | | | | |
| | STA | 324 | 100 | | | |
| | BPADA | 344 | | 100 | | |
| | APG700 | 404 | | | 100 | |
| | UP-1 | 1600 | | | | 100 |
| Photoinitiator | HCHPK | | 2 | 2 | 2 | 2 |
| Temperature in light-shielded portion(° C.) | | | 117 | 115 | 100 | 92 |
| Length of cured product in unirradiated portion (mm) | | | 0.5> | 0.5> | 0.5> | 0.5> |

The foregoing description of the preferred embodiments of the present invention has been presented for purposes of illustration and description; however, it is not intended to be exhaustive or to limit the present invention to the precise form disclosed, and modifications and variations are possible as long as they do not deviate from the principles of the present invention.

The invention claimed is:

1. A method for curing a (meth)acrylate composition, the composition comprising a first compound having one or more vinyl groups in a molecular structure thereof, the compound having a ratio of a molecular weight thereof to a number of the vinyl groups of 300 or lower, the composition not comprising a thermal polymerization initiator or a chain transfer agent, the method comprising a step of curing the composition without agitating the composition, wherein a portion of the composition that is not irradiated with light reaches a temperature from 151 to 175° C. as a result of photopolymerization of the composition and is cured by thermal polymerization caused by a heat of reaction generated during said photopolymerization.

2. The method according to claim 1, wherein the composition further comprises one or more vinyl group-containing compounds other than the first compound, including a second compound having one or more vinyl groups in a molecular structure thereof, the second compound having a ratio of a molecular weight thereof to a number of the vinyl groups higher than 300, and a content of the first compound with respect to a total content of all vinyl group-containing compounds in the composition is 30 mass % or higher.

3. The method according to claim 2, wherein the composition further comprises 0.1 to 20 mass % of a photopolymerization initiator with respect to a total mass of the composition.

* * * * *